United States Patent [19]

Trees

[11] Patent Number: Plant 7,641

[45] Date of Patent: Sep. 3, 1991

[54] VARIETY OF GERANIUM NAMED RED SATISFACTION

[75] Inventor: Scott C. Trees, Elburn, Ill.

[73] Assignee: Geo J. Ball, Inc., West Chicago, Ill.

[21] Appl. No.: 519,298

[22] Filed: May 4, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden Ziesenheim & Webb

[57] ABSTRACT

A new cultivar is characterized by its bright scarlet color which shows little sign of burn under high light and temperature conditions. The medium green foliage forms a compact mound shape with the bloom placed just above the canopy. The variety also branches very freely producing an abundance of cuttings.

1 Drawing Sheet

BACKGROUND OF THE INVENTION

The present invention comprises a new and distinct cultivar of *Pelargonium*×*hortorum* known by the varietal name Red Satisfaction (Oglevee No. 301, PAS No. 797A/84). The new variety wa discovered in a selective breeding program by Mr. Scott Trees in April of 1984 in West Chicago, Ill. The new variety is a selection from the crossing of a $F_1$ Semidouble of Bright Scarlet by Kim (U.S. Plant Pat. No. 5,311).

The new variety was first asexually reproduced by cuttings at Pan American Seed Company in West Chicago, Ill. following its discovery. The new variety has been repeatedly asexually reproduced by cuttings at Oglevee Ltd. in Connellsville, Pa. It has also been trial and field tested in the summers of 1987 and 1988 and has been found to retain its distinctive characteristics through successive propagations.

The new variety has more scarlet tones and is a taller plant when compared to its patented parent Kim.

The new cultivar when grown in a glass greenhouse in Connellsville, Pa. using natural light and 60° F. (night), 68° F. (day), and 71° F. (vent) has a response time of 6 weeks from a rooted cutting to flowering in a 10 centimeter pot. This response time was determined on plants grown in a soilless media employing constant fertilizer of 200 to 250 parts per million of nitrogen and potassium and in full light.

DESCRIPTION OF THE DRAWING

FIG. 1 of the accompanying photographic drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by Oglevee Ltd. Connellsville, Pa. The plant history was taken on six week plants potted on Feb. 17, 1989 and flowered on Apr. 3, 1989, blossomed under natural light in a greenhouse and color readings were taken indoors under 200–220 foot candles of cool, white fluorescent light. Color references are primarily to the R.H.S. Colour Chart of The Royal Horticultural Society of London.

THE PLANT

Classification:
- *Botanical.*—*Pelargonium*×*hortorum.*
- *Commercial.*—Zonal Florists Geranium.

Form: Compact; free and early flowering, basal branching, uniform mound.

Height: 20–24 cm above media surface.

Growth: Compact mound habit; free basal branching, free and early flowering.

Strength: Stands upright without artificial support.

Foliage: Stalked leaf attachment; little or no zoning present.

Leaves:
- *Size.*—8–11 cm (fully expanded leaf).
- *Shape.*—Reniform; cordate base.
- *Margin.*—Crenate.
- *Texture.*—Slightly pubescent, slightly reflective.
- *Color.*—Top: Green Group 137B. Bottom: Green Group 137C.
- *Ribs and veins.*—Palmate venation; Color: Yellow-Green Group 146C.

Petioles: 5.5–7.5 cm in length.
- *Color.*—Yellow-Green Group 146C.

Stem:
- *Color.*—Yellow-Green Group 146D.
- *Internodes.*—4.5–5.0 cm in length.

THE BUD

Shape: Upright hemispherical cluster.

Size: 3.5–5.5 cm across.

INFORESCENCE

Blooming habit: Semi-double; hemispherical, slow to shatter.

Size: 10–12 cm across.

Borne: Umbel; floret on pedicel; pedical on peduncle; 2.6 cm above foliage canopy.

Florets:
- *Form.*—Flat to slightly cupped; with pediloids; obovate.
- *Color.*—Front: Red Group 43A. Eye: Red Purple Group 61C. Back: Red Group 43B.
- *Petals.*—9–11 in number; separate, not united; margin entire; obovate; smooth; flat to slightly cupped.
- *Size.*—4.0–5.0 cm across.

*Texture and appearance.*—Smooth; from a distance bloom color appears a bright scarlet accented with medium green foliage.

Petaloids:

*Quantity.*—3 to 5 in number.

*Shape.*—Narrow, elongated twisted.

*Color.*—Front: Red Group 43A. Back: Red Group 41A.

Pedicel:

*Length.*—4.0–4.5 cm in length.

*Color.*—Base: Yellow-Green Group 146C (peduncle end). Tip: Red-Purple Group 59B (stipule end).

Peduncle: Arises from the node opposite leaf petiole.

*Color.*—Yellow-Green Group 146B.

*Length.*—14 to 20 cm.

Disease resistance: Not known.

Lasting quality: This variety has been field tested and has proven to be very heat tolerant. The bright scarlet red bloom color shows little sign of burn and the foliage stands up extremely well.

REPRODUCTIVE ORGANS

Stamens:

*Anthers.*—2–3 mm in length.

*Filaments.*—5–8 mm in lengths; white to pale pink; some irregular in shape.

*Pollen.*—Golden brown.

Pistils:

*Number.*—1; 5–7 parted stigma.

*Length.*—10–11 mm in length.

*Stigma.*—5–7 parted, Red-Purple.

*Style.*—1; 2–3 mm in length, Red-Purple.

Ovaries: Superior; pale green; very pubescent; 5–6 mm in length.

Fruit: None observed.

The bright scarlet color is an improvement over the current varieties in this class in that it is less likely to show petal burn in higher light and temperature conditions. The medium green foliage forms a compact mound shape with the bloom placed just above the canopy. The variety also branches very freely producing an abundance of cuttings. This variety is pleasing to the grower in view of its earliness, more cutting production and compactness and is pleasing to the home gardener because of the heat tolerance, color and improved garden life.

I claim:

1. A new and distinct variety of Geranium plant substantially as shown and described.

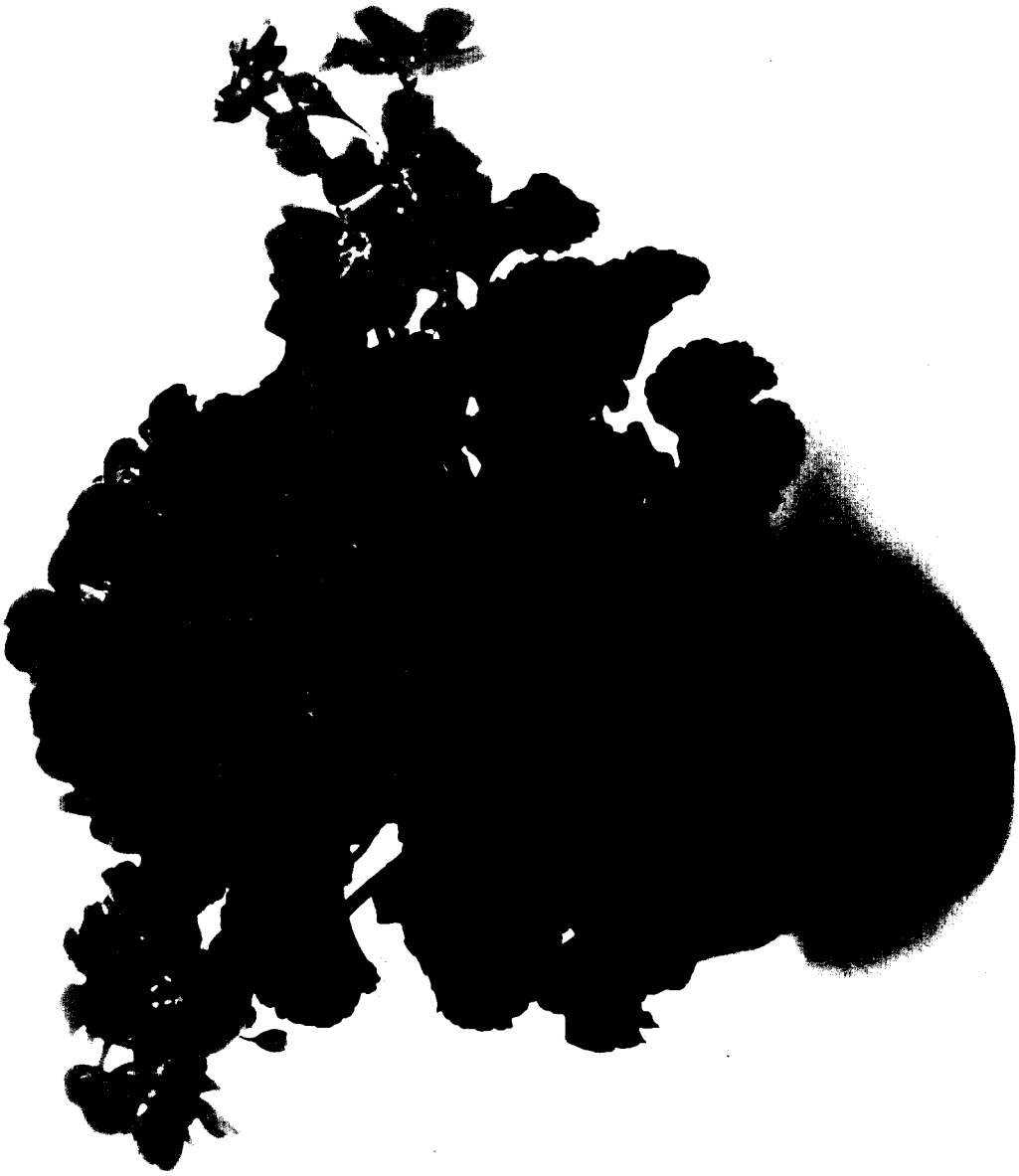

* * * * *